(12) United States Patent
Getsla et al.

(10) Patent No.: US 6,865,409 B2
(45) Date of Patent: Mar. 8, 2005

(54) SURFACE ELECTROMYOGRAPHIC ELECTRODE ASSEMBLY

(75) Inventors: Robert M. Getsla, San Jose, CA (US); Victor F. Simonyi, Berkeley, CA (US)

(73) Assignee: Kinesense, Inc., Berkeley, CA (US)

( * ) Notice: Subject to any disclaimer, the term of this patent is extended or adjusted under 35 U.S.C. 154(b) by 25 days.

(21) Appl. No.: 10/292,394

(22) Filed: Nov. 7, 2002

(65) Prior Publication Data

US 2003/0120329 A1 Jun. 26, 2003

Related U.S. Application Data

(60) Provisional application No. 60/338,265, filed on Nov. 7, 2001.

(51) Int. Cl.[7] .............................................. A61B 5/0492
(52) U.S. Cl. ........................ 600/393; 600/546; 128/902
(58) Field of Search ................................ 600/391–393, 600/546; 128/902

(56) References Cited

U.S. PATENT DOCUMENTS

| | | | | |
|---|---|---|---|---|
| 3,880,146 A | * | 4/1975 | Everett et al. | 600/523 |
| 4,122,843 A | * | 10/1978 | Zdrojkowski | 600/382 |
| 4,155,354 A | * | 5/1979 | Rasmussen | 600/393 |
| 4,763,660 A | * | 8/1988 | Kroll et al. | 600/391 |
| 4,865,039 A | | 9/1989 | Dunseath, Jr. | |
| 5,341,806 A | * | 8/1994 | Gadsby et al. | 600/393 |
| 6,643,541 B2 | * | 11/2003 | Mok et al. | 600/546 |
| 2002/0019588 A1 | * | 2/2002 | Marro et al. | 600/383 |

* cited by examiner

Primary Examiner—Lee S. Cohen
(74) Attorney, Agent, or Firm—Beyer Weaver & Thomas LLP

(57) ABSTRACT

An electrode assembly for use on a surface of biological tissue to measure bio-electric signals including an electrode apparatus having an electrode device adapted to directly contact the surface of the biological tissue. The electrode apparatus receives and transmits bio-electric signals measured across the biological tissue having a first voltage and a minute first current. A signal transmission line is included having a signal transmission conductor electrically coupled at one portion to the electrode device for transmission of the bio-electric signals. The transmission includes a second conductor electrically coupled to the amplifier apparatus and arranged to substantially shield the transmission conductor from ambient electric fields generated from sources external to the transmission line. A high impedance amplifier device is included having a signal input and a signal output. The signal input is electrically coupled to another portion of the signal transmission conductor for receipt of the transmitted bio-electric signals. The signal output is electrically coupled to the shield conductor, in a feedback loop, for receipt of at least a portion of the transmitted bio-electric signals, such that the voltage of the signals at the signal input of the high impedance amplifier device is maintained substantially equal to the voltage of the signals output from the signal output thereof.

27 Claims, 4 Drawing Sheets

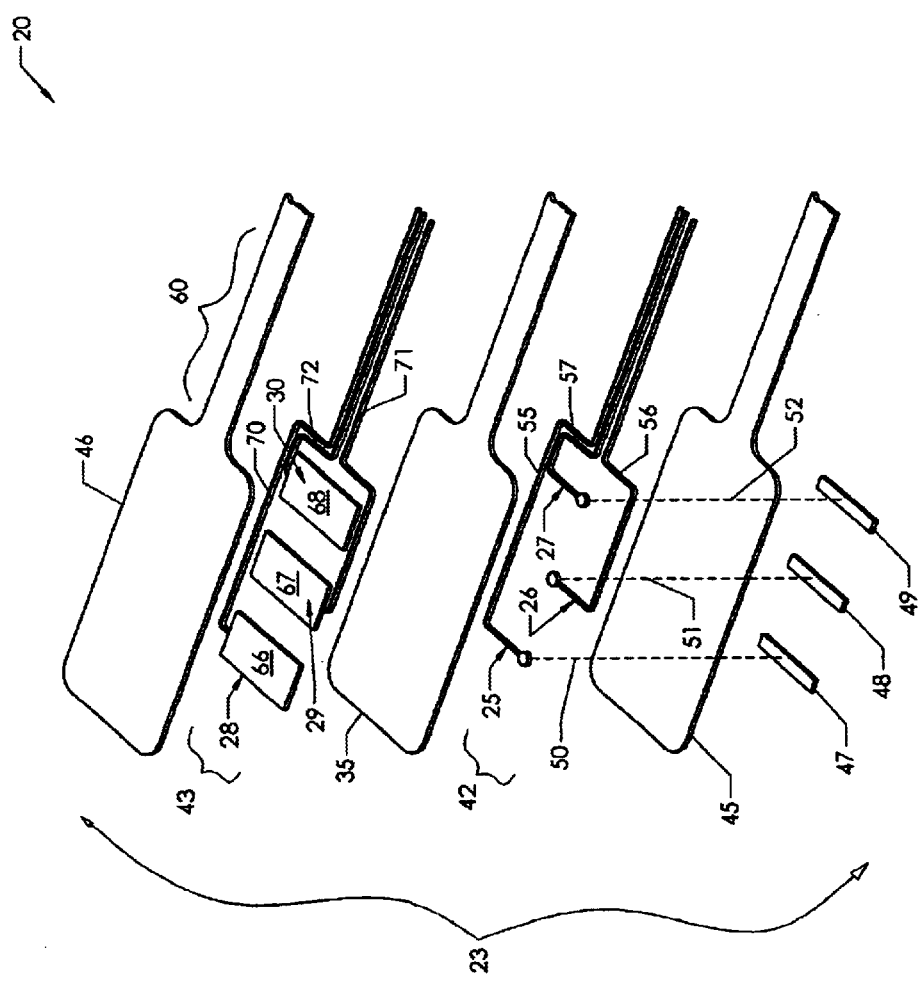
FIG._1

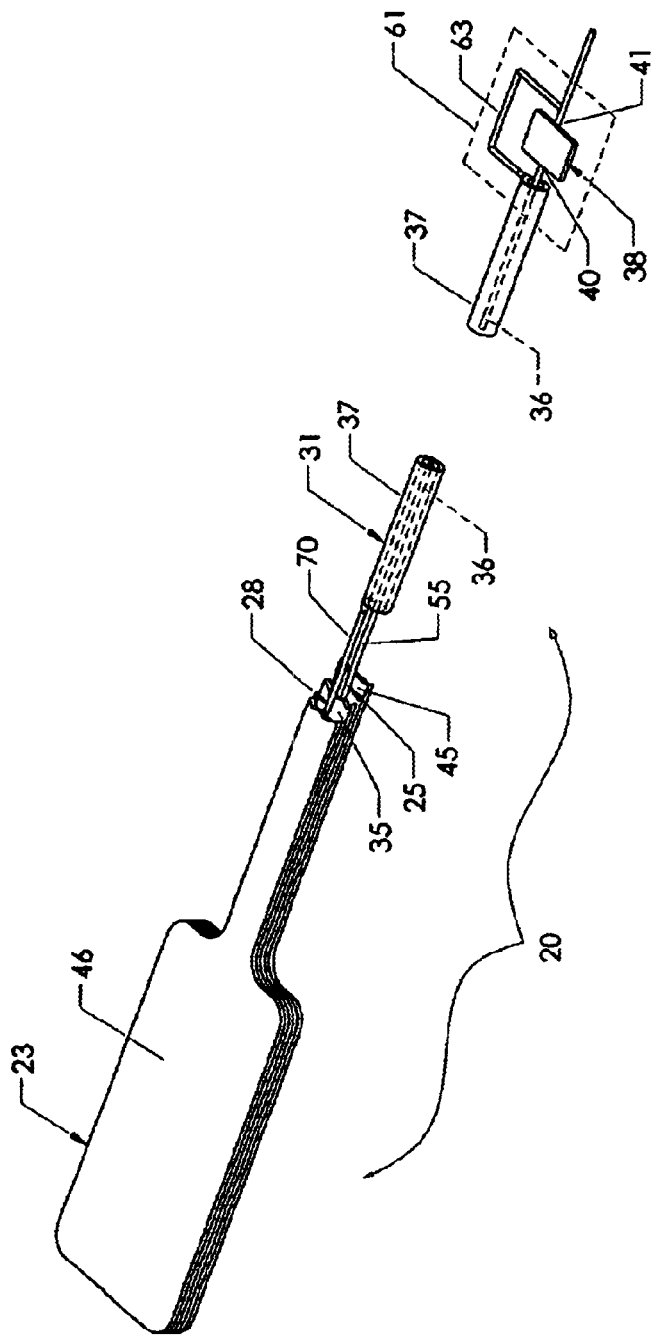
FIG._2

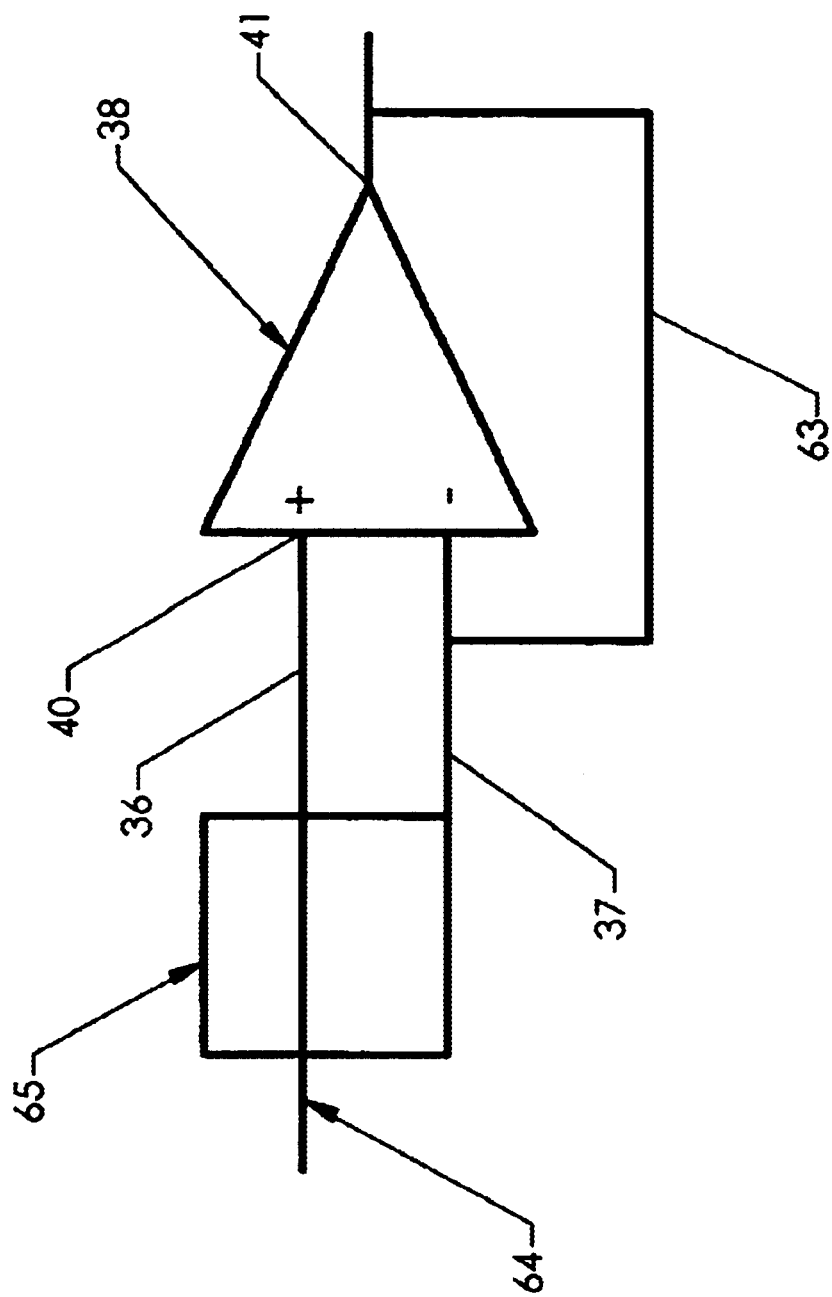
FIG._3

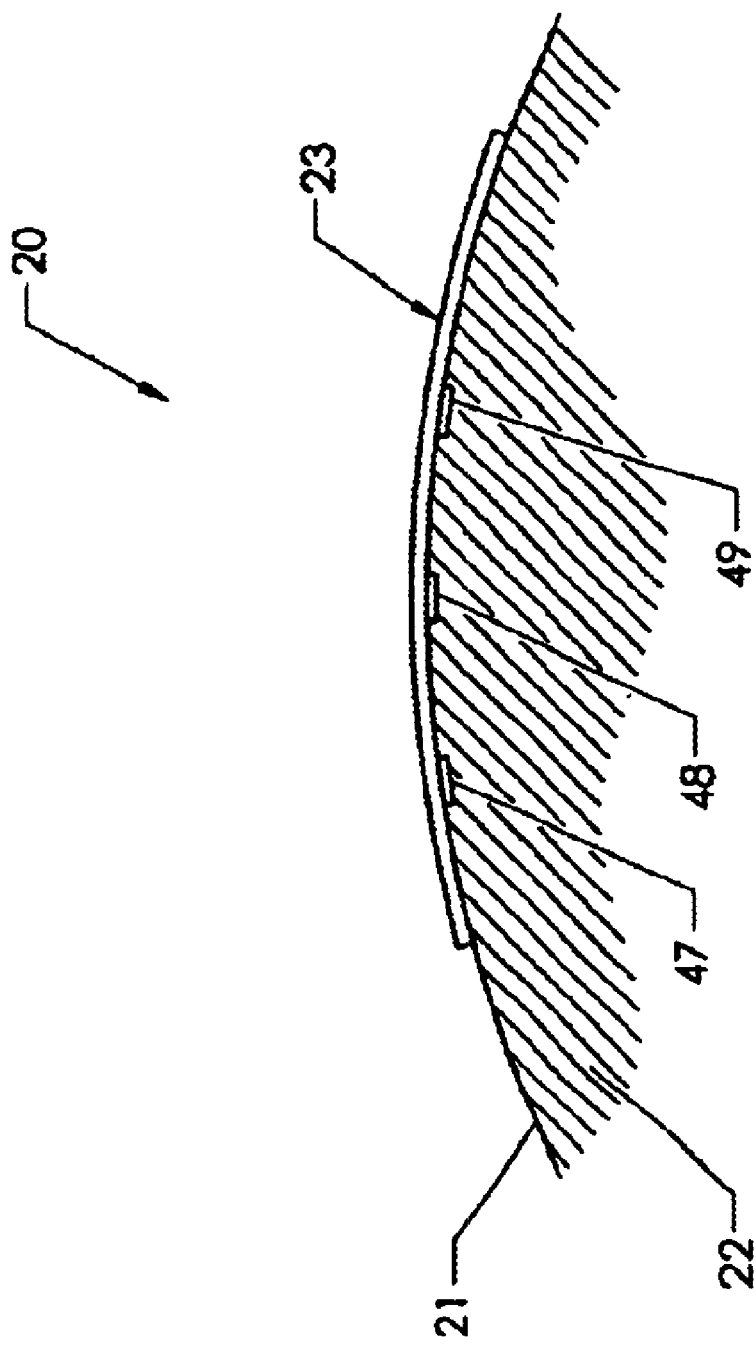
FIG_4

SURFACE ELECTROMYOGRAPHIC ELECTRODE ASSEMBLY

RELATED APPLICATION DATA

This application claims priority under 35 U.S.C. §119 to U.S. Provisional Application Ser. No. 60/338,265, filed Nov. 7, 2001, naming Getsla et al. inventors, and entitled SURFACE ELECTROMYOGRAPHIC ELECTRODE ASSEMBLY, the entirety of which is incorporated herein by reference in its entirety for all purposes.

TECHNICAL FIELD

The present invention relates, generally, to surface mounted electrode assemblies for measuring bioelectric signals, and specifically to surface mounted electromyographic electrodes assemblies.

BACKGROUND ART

Surface electromyography electrode assemblies have a variety of industrial uses. Their primary application, however, is concentrated in the psychological, academic research and medical professional fields. For example, psychologists use EMG biofeedback to help patients learn to relax certain muscles, as an aid in overall relaxation. Academic researchers, on the other hand, use EMG measurements to study the impact of muscle contractions on human movement and biomechanics.

Medical professionals employ EMG biofeedback to help patients retrain damaged or atrophied muscles. This can include those recovering from neurological damage as well as those recovering from prolonged inactivity (e.g. post surgery).

Such retraining can be difficult, in part, because the human body will often engage and strengthen surrounding undamaged muscles as substitutes for damaged muscles in order to protect the damaged muscle from re-injury. This can be particularly problematic when the patient is not able to "sense" which muscle is contracting, the injured muscle or the one being substituted.

For example, the Vastus Medialis Oblique (VMO) and Vastus Lateralis (VL) muscles are both part of the quadriceps or "thigh" muscle group. Both muscles attach to the patella, or "kneecap". Both muscles contract when a seated patient raises his/her leg from the perpendicular (to the ground) to the horizontal (fully extended) position. However, in addition to pulling the patella in the proximal (toward the hip joint) direction, these two muscles also pull in the medial (toward the midline of the body) and lateral (away from the midline of the body) directions. When the forces of these medial and lateral pulls are balanced, the patella "tracks" along its groove at the distal (away from the hip joint) end of the femur without excess wear on either side. Patients often have difficulty consciously choosing the relative amount of contraction between these two muscles.

When one of these two muscles is atrophied, for example the VMO, the body protects the atrophied muscle by over-utilizing a substitute, in this case the VL. As a result, the patella is pulled to one side, causing excessive wear. In addition, this substitution pattern tends to defeat the purpose of therapeutic exercises: instead of strengthening the targeted muscle (VMO) it can serve to increase the strength of the substituted VL muscle instead. The application of EMG biofeedback, however, has been shown to improve the patient's ability to perform their exercises while avoiding the muscle substitution effects.

Surface EMG

Surface EMG devices work by measuring, from the surface of the body, the electrical potential that develops across the surface of a muscle as it contracts. This potential is related to the force of the muscle contraction (i.e., as the muscle produces more force, either by increasing the contraction of its fibers or by contracting more of its fibers, the electrical potential increases, and vice versa).

Since differential amplification is employed in every design, at least two electrodes and a reference electrode are required directly over the muscle. In addition, some form of electrode isolation is required to prevent shorting of the signal between electrodes.

The impedance at the surface of the body can be quite high if the skin is dry enough. Localized skin condition variations, furthermore, can result in significant changes in impedance. Consequently, these changes interfere with the accurate measurement of the source signal by adding voltage variations that are not the result of muscle activity.

Attempts to alleviate these two problems stated above have required either increasing the overall impedance of the entire signal path or lowering and stabilizing the impedance at the skin surface. In the former case, by increasing the overall impedance of the entire signal path, the remaining impedance changes at the skin become insignificant as a percent of the overall signal path impedance. More commonly, in the latter case, the impedance at the skin surface is lowered and stabilized by applying an artificial conducting medium, usually in a gel or paste form, to the contact points

Conductive Paste or Gel

The current designs require that, under some or all circumstances, an artificial conductive medium be applied to the contact points in order to lower the impedance at the surface of the body and minimize the effects of body surface impedance changes. This conductive medium is always in the form of conductive paste or gel applied individually to each contact point so as not to cause signal shorting between contact points. Snap on electrodes can be purchased which are specifically designed to address this problem.

However, this arrangement increases cost, is inconvenient, and will not properly function in environments where the moisture content is high. In these latter situations, the signal is shorted where the naturally occurring skin environment creates highly conductive aqueous "bridges" between contact areas. For instance, such aqueous bridges are formed when the electrode is immersed in water, such as in the pool, or when perspiration is heavy.

It would be desirable, therefore, to provide an electrode that functions in all skin environments, and eliminates or requires minimal surface preparation.

High Impedance Signal Path

Increases in amplifier impedance have greatly reduced the sensitivity of the pickup to changes in impedance between the signal source (muscle) and the amplifier. This higher impedance, however, increases the "antennae" effect (capacitive coupling) that can occur if the signal travels along wiring between the electrode and the amplifier. This antennae effect makes the electrode assembly, (including the cable), collect and pass on unwanted signals from nearby electrical fields (e.g. overhead lighting, etc.).

Electrical fields, such as those emanating from fluorescent lighting fixtures, will induce small alternating currents in any available conductors through capacitive effects. This small induced current will create a significant voltage change along a high impedance signal path, significantly altering the signal to be measured. In effect, any conductor can act like one "plate" of a capacitor where it comes in contact with the electrical field generated by the fluorescent light bulb or electrical power wiring. For the low frequencies being measured in biological organisms, the impedance resisting the resulting ac current arises out of the reactive capacitance of the conductor's signal path.

Current designs solve this problem by applying a "pre-amplification" approach, that place an initial buffering amplifier at the pickup site. This assembly converts the high impedance source to a low impedance output for transmission along a wire. However, these designs lead to electrode assemblies that are rigid, bulky, cumbersome, expensive to manufacture and sensitive to heat and moisture.

It would be desirable, therefore, to design a high impedance electrode assembly that minimized the "antennae" effect without active amplification at the pickup site.

DISCLOSURE OF THE INVENTION

The present invention provides a flexible, surface electromyographic electrode apparatus for use on a surface of biological tissue to measure bio-electric signals thereof. The electrode apparatus includes a first conductive electrode device adapted to directly contact the surface of the biological tissue to receive and transmit bio-electric signals. A first conductive guard device is positioned substantially adjacent and substantially over the electrode device such that the measured bio-electric signal passing therethrough is substantially shielded from ambient electric fields generated from sources (for example, fluorescent lighting) external to the electrode apparatus. The electrode apparatus further includes a substantially non-conductive, flexible, sheet materials positioned between, above and below the electrode device and the guard device to substantially prevent conductive contact therebetween.

Accordingly, this electrode apparatus provides an interference resistant, high impedance signal path, exhibiting little or no antennae effect without the need for active amplification at the pickup site. Since no active electronic components are present in or near the electrode apparatus itself, a uniformly, substantially flexible surface electrode apparatus can be constructed that can easily conform to body contours, significantly increasing its application.

In one specific embodiment, the conductive electrode device includes a surface contact portion adapted to directly contact the surface of the biological tissue at the bottom exposed surface of the electrode apparatus, and a signal transmission portion disposed between the sheet materials. The contact portion is electrically coupled to the signal transmission portion through a conductive lead to conduct the signal along the electrode device.

In another configuration, the contact portion of the electrode device includes a contact footprint, and the signal transmission portion of the electrode device includes a signal transmission footprint. The guard device, disposed between the sheet materials, includes a guard conductor portion having a guard conductor footprint, and a shield conductor portion having a shield conductor footprint. The guard device being positioned and oriented such that when the electrode apparatus is operably mounted on the biological tissue, the guard conductor footprint of the guard conductor portion at least extends over the contact footprint of the electrode contact portion, and the shield conductor footprint of the shield conductor portion at least extends over the signal transmission footprint of the electrode signal transmission portion.

In another aspect of the present invention, an electrode assembly is provided for use on a surface of biological tissue to measure bio-electric signals thereof. The electrode assembly includes an electrode apparatus having an electrode device adapted to directly contact the surface of the biological tissue to receive and transmit bio-electric signals sensed from the biological tissue having a first voltage and a minute first current. A shielded signal transmission line is included having a signal transmission conductor electrically coupled at one portion to the electrode device for transmission of the bio-electric signals. The transmission includes a shielded conductor electrically coupled to the electrode apparatus and arranged to substantially shield the transmission conductor from ambient electric fields generated from sources external to the transmission line. A high impedance amplifier device is included having a signal input and a signal output. The signal input is electrically coupled to another portion of the signal transmission conductor for receipt of the transmitted bio-electric signals. The signal output is electrically coupled to the shield conductor, in a feedback loop, for receipt of at least a portion of the transmitted bio-electric signals, such that the voltage of the signals at the signal input of the high impedance amplifier device is maintained substantially equal to the voltage of the signals output from the signal output thereof.

In one specific embodiment, the high impedance amplifier has a relatively high input impedance in the range of about $10^8$ ohms to about $10^{10}$ ohms.

In another configuration, the electrode assembly further includes a low impedance amplifier device having a signal input and a signal output. The signal input of the low impedance amplifier is electrically coupled to the signal output of the high impedance amplifier device for receipt of substantially the remaining portion of the transmitted bio-electric signals. The high impedance amplifier and the low impedance amplifier have relative high and low impedance, respectively, such that the bio-electric signals delivered from the output of the high impedance amplifier have a second current increased over the first minute current, and a second voltage substantially similar to the original first voltage of the original bio-electric signals.

In yet another aspect of the present invention, an electromyographic surface electrode assembly is provided for use on a surface of biological tissue to measure bio-electric signals thereof. The electrode assembly includes a flexible, surface electromyographic electrode apparatus including a conductive electrode device adapted to directly contact the surface of the biological tissue to receive and transmit bio-electric signals sensed from the biological tissue having an original first voltage and an original minute first current. The electrode apparatus includes a conductive guard device positioned substantially adjacent and substantially over the electrode device such that the measured bio-electric signal passing therethrough is substantially shielded from ambient electric fields generated from sources external to the electrode apparatus. A substantially non-conductive, flexible, first sheet material is positioned between the electrode device and the guard device to substantially prevent conductive contact therebetween. The surface electrode assembly further includes a co-axial cable having an inner conductor and an outer conductor shielding the inner conductor. At one end of the co-axial cable, the inner conductor is electrically coupled to the electrode device for transmission of the bio-electric signals, while the outer conductor is electrically coupled to the guard device to substantially shield the signal transmitted along the inner conductor from the ambient electric fields generated from sources external thereto. At the opposite termination end of the co-axial cable is a buffer amplifier device having a signal input and a signal output. The signal input is electrically coupled to the inner conductor of the co-axial cable for receipt of the transmitted bio-electric signals, while the signal output is electrically coupled to the outer conductor of the co-axial cable, in a feedback loop. Thus, at least a portion of the transmitted bio-electric signals is received by the outer conductor, such that the voltage of the signals at the signal input of the high impedance amplifier device is maintained substantially equal to the voltage of the signals output from the signal output thereof.

Accordingly, the collective electrode assembly of the present invention completes an outer "guard" circuit that protects the signal transmission circuit or conductor from contamination by ambient electrical fields.

In one specific configuration, the electrode apparatus includes a number of conductive electrode devices each adapted to directly contact the surface of the biological tissue, at locations spaced-apart from one another. Each electrode device is adapted to receive and transmit respective bio-electric signals. Further, this design includes a number of conductive guard devices each positioned substantially adjacent and substantially over a respective, corresponding conductive electrode device such that the respective measured bio-electric signals passing therethrough are substantially shielded from ambient electric fields generated from the sources external to the electrode apparatus. The first sheet material is positioned between the number of conductive electrode devices and the number of conductive guard devices to substantially prevent conductive contact therebetween.

Each conductive electrode device includes a respective contact portion adapted to directly contact the surface of the biological tissue, and a respective signal transmission portion carrying the respective bio-electric signals and electrically coupled to the respective contact portion thereof.

BRIEF DESCRIPTION OF THE DRAWING

The assembly of the present invention has other objects and features of advantage which will be more readily apparent from the following description of the best mode of carrying out the invention and the appended claims, when taken in conjunction with the accompanying drawing, in which:

FIG. 1 is an exploded perspective view of a flexible surface electromyographic electrode apparatus of an electrode assembly constructed in accordance with the present invention.

FIG. 2 is a schematic diagram of the electrode assembly of the present invention.

FIG. 3 is a schematic diagram of a "guard" circuit of the present invention.

FIG. 4 a cross-sectional view of the electrode apparatus of FIG. 1 operably mounted to biological tissue.

BEST MODE OF CARRYING OUT THE INVENTION

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–4, an electromyographic (EMG) surface electrode assembly, generally designated 20, is illustrated for use on a surface 21 of biological tissue 22 to measure bio-electric signals thereof. The electrode assembly 20 includes a flexible, surface electromyographic electrode apparatus 23 having a number of conductive electrode devices 25–27, a number of corresponding conductive guard devices 28–30 and a substantially non-conductive, flexible, first sheet material 35 positioned between the electrode devices and the guard devices to substantially prevent conductive contact therebetween. Each of the electrode devices 25–27 are adapted to directly contact the surface of the biological tissue 22, at spaced-apart locations, to receive and transmit bio-electric signals measured sensed from the biological tissue 22. Each respective signal having an original respective first voltage and an original respective minute first current. Regarding the corresponding conductive guard devices 28–30, each being positioned substantially adjacent and substantially over a corresponding electrode device 25–27, respectively, such that the respective measured bio-electric signal passing therethrough is substantially shielded from ambient electric fields generated from sources external to the electrode apparatus.

In accordance with the present invention, the electromyographic surface electrode assembly 20 further includes a number of respective shielded signal transmission lines 31 each having a corresponding signal transmission conductor 36 and shield conductor 37, only one of which is shown and described in FIG. 2. In fact, for clarity, only one electrode assembly 20 will generally be described in detail, although each such electrode contains like components. FIG. 2 best illustrates that the signal transmission conductor 36, at one portion thereof, is electrically coupled to the corresponding electrode device 25 of the electrode apparatus 23 for transmission of the bio-electric signal, while the shield conductor 37 is electrically coupled to the guard device 28. This arrangement functions to continuously shield the transmitted bio-electric signal from the ambient electric fields as it travels along the signal transmission conductor 36.

The electromyographic surface electrode assembly 20 further includes a high impedance, first stage amplifier device, generally designated 38, having a signal input 40 and a signal output 41 (FIGS. 2 and 3). The signal input 40 is electrically coupled to the signal transmission conductor 36 of the transmission line 31, at another portion thereof, for receipt of the transmitted bio-electric signals. The signal output 41 of the first stage amplifier device, on the other hand, is electrically coupled to the shield conductor 37 of the transmission line 31, in a feedback loop, for receipt of at least a portion of the transmitted bio-electric signals. In this arrangement, the voltage of the signals-at the signal input 40 of the high impedance, first stage amplifier device 38 is maintained substantially equal to the voltage of the signals output from the signal output thereof.

Accordingly, the electrode assembly of the present invention completes an outer "guard" circuit that protects the signal transmission circuit or conductor 36 from contamination by ambient electrical fields (for example, caused by fluorescent lighting, electrical wiring, etc.). This enables an interference resistant high impedance signal path with little or no antennae effect without the need for active amplification at the pickup site. As will be described in greater detail below, the physical absence of an active amplifier enables the construction of a uniformly, substantially flexible surface electrode apparatus that can easily conform to body contours. Further, since no active electronic components are present in or near the electrode apparatus itself, this electrode design is less expensive to manufacture than pre-amplified designs.

Another advantage of this EMG electrode assembly is that the application of a relatively high impedance amplifier will also result in a very low current along the signal path leading to (but not including) the signal input to the high impedance, first stage amplifier device. The signal path leading to the signal input to the amplifier device itself can therefore be relatively high impedance (e.g., in the range of between about $10^4$ ohms to about $10^6$ ohms, compared to the impedance requirements of other designs) without producing a significant voltage drop across the amplifier. This approach will therefore increase significantly the range of materials that can be used, including non-metals, to effectively and efficiently carry the signal from the source to the amplifier device.

Referring back to FIG. 1, this electrode apparatus 23 of the electrode assembly 20 is preferably provided by a sandwich of two conductive circuitry layers 42, 43 (i.e., first circuit layer 42 containing the conductive electrode devices 25–27, and second circuit layer 43 containing the conductive guard devices 28–30) with an insulative layer 35 (i.e., the flexible first sheet material) disposed therebetween to prevent conductive contact. Thus, the conductive second circuit layer 43 containing the guard devices 28–30 does not make contact with the user's skin or with any of the conductive material of the Signal Path circuitry (FIGS. 1 and 2). To further electrically isolate the first circuit layer 42, a second substantially non-conductive, flexible, insulative layer (second sheet material 45) is disposed adjacent to and in contact with the first sheet material 35, enclosing the first circuit layer 42 therebetween. This sandwich arrangement substantially prevents inadvertent conductive contact with the first circuit layer 42, as well as substantially prevents short circuiting between the conductive electrode devices by positioning the insulative materials between the circuits. Similarly, a third substantially non-conductive, flexible, insulative layer (third sheet material 46) is disposed adjacent to and in contact with the first sheet material 35 along an upper surface thereof to enclose the second circuit layer 43 therebetween. This sandwich arrangement, likewise, substantially prevents inadvertent conductive contact with the second circuit layer 43, as well as substantially prevents short circuiting between the conductive guard devices 28–30 by positioning the insulative materials between the circuits.

To provide conductive contact with the surface of biological tissue 22, the conductive electrode devices 25–27 each include a corresponding surface contact portion 47–49, respectively at the exposed bottom of the second sheet material which are adapted to directly contact the target tissue. Corresponding conductive leads 50–52 extend through the insulative second sheet material 45 to provide electrical coupling with a signal transmission portion 55–58 of the respective conductive electrode device 25–27 contained solely within the first circuitry layer 42. Hence, collectively, each conductive electrode devices includes the contact portion 47, the signal transmission portion 55 and the conductive lead 50 therebetween.

As best viewed in FIGS. 1 and 4, these thin surface contact portions 47–49 of the electrode devices 25–27 are spaced-apart along the bottom exposed surface of second sheet material 45. While these contacts are illustrated as elongated rectangular-shaped strips, it will be appreciated that the may be any shape. However, it will also be appreciated that the contact portions, as well as their corresponding conductive leads and signal transmission portions 55–58 do not conductively contact any portion of the other electrode devices. Further, it will be understood that the non-conductive, sheet materials are disposed sufficiently between the conductive electrode devices 25–27 to prevent such shorting. In one example, the spacing between the adjacent contact portions 47–49 and/or signal transmission portions 55–58 may be as little as about 1 mm to about 1 cm.

Such sheet-like materials that provide non-conductive and flexible properties, as well as sufficient electrical isolation are abundant. However, it is also preferable that such materials be substantially impervious to moisture, and bio-compatible, of course. Examples of these materials include, but are not limited to various kinds of plastic or silicone compounds.

Regarding the composition of the circuitry layers 42 and 43, including the surface contact portions 47–49, these materials of course must be conductive in nature. Common circuitry materials such as thin strips of metal or some other conductive material may be applied. However, since the circuit can still be a very high impedance circuit, it is not necessary for these circuitry layers conductor sections to be highly conductive materials. So, for example, the conductive sections could be made of conductive silicone, conductive plastics or other metal or non-metal materials of various conductivities that may enhance flexibility. Accordingly, such materials may be easily integrated, molded, adhered, etc. to the insulated sheet materials to essentially form a unitary fabrication. Another advantage of the invention is that it allows for an EMG electrode design that removes the need to use any metals as part of surfaces that will have direct contact with the user's skin. This will eliminate skin allergy problems associated with some metals such as nickel.

Further, the conductive material of the surface contact portions 47–49 and/or the corresponding conductive leads 50–52 of the conductive electrode devices 25–27 need not be the same material as either of the other conductive layers. For instance, the contact portions of the electrode devices may be composed of a more bio-compatible, conductive silicon material, while the corresponding signal transmission portions may be comprised of a metallic material. Also, the conductive leads 50–52 need not be of the same material as the other conductive material.

The five layers (i.e., circuitry layers 42, 43 and sheet material layers 35, 45 and 46) are bonded to each other to make a robust assembly that is impervious to moisture. Examples of suitable adhesives to adhere the sheet material to one another, while maintaining sufficient flexibility, include, but are not limited to, silicon rubber cements. Collectively, a ribbon like flexible electrode structure is fabricated which can be operably mounted directly to the surface of moving muscular tissue. Accordingly, not only does the present invention provide a flexible EMG electrode apparatus 23 that can be shaped to fit or adhere to any body contour, but it also enables it to be imbedded in or attached to the inside of articles of clothing, without changes in appearance or comfort. It is even permissible to retain this device in the clothing during washing thereof.

Still another advantage of the invention is that it allows for a flexible electrode apparatus 23 that can be of any length, with the electrodes clustered at one end. In effect, the electrode assembly may replace some of the shielded cable transmitting the signal to the processing circuitry. Such a design will enhance the electrode assembly's ability to A) be incorporated in clothing and/or B) body contour.

In accordance with another aspect of this design, the contact portions 47–49 are mounted or attached to the bottom exposed surface of the second sheet material 45 in a manner protruding slightly therefrom. Thus, when the electrode apparatus 23 is held in place over the tissue surface 21 (FIG. 4), the subject's tissues "fills in the spaces" between the adjacent contact portions 47 and 48, and 48 and 49, providing a barrier to any signal "shorting" effects that might occur in the presence of moisture. The principle at work here is that conductivity through a salt solution (e.g. sweat, chlorinated pool water) is a function of the volume of the liquid between the electrodes; and that by pressing the electrode assembly against the skin, the volume of liquid surrounding the electrodes becomes vanishingly small. This approach, accordingly, relies on pressure rather than the viscosity of the conducting medium to ensure that no "bridging" between electrodes occurs. Such pressure may be applied, for instance, by elasticized fabric such as Spandex™.

This electrode design enables the fabrication of a flat, flexible electrode assembly structure that performs equally well whether the user is on land, in water, or perspiring heavily since, under most circumstances, no specialized conductive medium is required. This is not so of the current electrode designs which require a viscous conductive medium between the tissue and the electrode to avoid shorting between electrodes.

This electrode design relies on natural skin environments for the necessary conductivity at the skin surface. Accordingly, little or no skin preparation is required for proper functioning of the EMG electrode apparatus of the present invention. Only in circumstances where very dry skin creates very high skin impedance will any preparation be necessary, and then merely wetting the contact areas with any convenient aqueous solution—(e.g. tap water, saline, etc.) will be the only requirement. This approach will result in changes in the conductivity at the surface of the skin during and between applications. The impedance of the amplifier can be high enough, however, that the overall impedance of the circuit does not change materially. Therefore, the accuracy of the signal reading will not be materially affected.

A further advantage of the invention is that an EMG electrode can be built that is insensitive to heat, and can even be autoclaved for sterilization between uses.

As indicated above and as illustrated in FIG. 2, the signal transmission conductor 36 of each shielded signal transmission line 31 is electrically coupled to the signal transmission portion 55 of the corresponding electrode device 25 of the electrode apparatus 23, while the shield conductor 37 of the shielded signal transmission line 31 is electrically coupled to the corresponding guard device 28 thereof. Thus, as will be described in greater detail below, a shield transmission signal circuit is constructed for the entire circuit path from the contact portion 47 of the corresponding electrode device 25 to the first stage amplifier 38 thereof to shield the signal transmission conductor 36 from unwanted signals from nearby ambient electrical fields (e.g. overhead lighting, etc.).

In one embodiment, the shielded transmission line is provided by a co-axial cable having an inner signal transmission conductor 36 and an outer shield conductor 37. It will be appreciated, of course, that the shielded transmission line 31 can be any "shielded" line.

In another specific embodiment of the present invention, the shielded ribbon-like material electrode apparatus 23 containing the circuit layers 42, 43 may replace portions of the shield co-axial cable 31. For example, the electrode apparatus 23 may include an elongated neck or extension portion 60, as shown in FIGS. 1 and 2, extending between the shielded cable and the electrode area of the electrode assembly to transmit the signal for some distance rather than of the shielded cable. These elongated sections will generally not include contact portions of the electrodes apparatus, but may in some configuration. In other instances, the shielded ribbon-like extension portion 60 of the electrode apparatus 23 may replace the shielded cable at selected sections where the cable might hinder product design efforts. For example, to design a pair of knee length pants for someone who wants the muscle activity in the proximity of their knee measured might mean running shielded cable from the knee to an amplifying and processing unit at the waist. The connection between the electrode assembly and the shielded cable may be bulky and inconvenient near the knee as opposed to placing it at the user's waist. Extending the electrode assembly to carry the signal from the knee area to the waist would eliminate this particular problem.

It should be noted that the portion of the electrode assembly attached to the shielded cable at the end away from the first stage amplifier, while described above as constructed by combining thin sheets of alternating conductive and non-conductive material, may be manufactured from materials which can result in this end design without taking the intermediate form of separate sheets.

"Guard" Circuit Approach

The concept of an electrical "guard" has been heretofore used in conjunction only with very high impedance technical and industrial measuring instruments. These instruments' high impedance sensors and signal path must be protected from ambient electrical fields, because ambient electrical fields could induce noise and undesired signals into the rest of the circuitry, as above-indicated.

By replacing the original signal path with an electrical "guard", the circuit is significantly less sensitive to ambient electrical fields, and is further self adjusting to changes in voltage that are induced by these ambient electrical fields. Moreover, effective capacitance of the signal path is dramatically reduced in comparison to other approaches to protecting the signal path from external fields. This is performed by extending the output circuit from the first stage amplifier 38 along a path positioned between the source of ambient noise and the original signal path between the corresponding electrode device 25 and the first stage amplifier 38.

In accordance with the present invention, a respective high impedance first stage amplifier 38, inside a system control unit 61 (FIG. 2), is placed at the termination point of each electrode device's signal transmission conductor 36 of the corresponding signal transmission line 31. This first stage amplifier presents a high impedance signal path to the electrode device 25, but does not amplify the signal voltage coming from the electrode device. Rather, the first stage amplifier 38 amplifies the minute signal current from the electrode device 25 to a relatively much larger current while replicating very closely the original signal voltage. This amplified current drives a signal along a circuit path leading to a second stage, low impedance amplifier 62. The lower input impedance of this second and subsequent stages signal path allows the first stage amplifier 38 to increase the current without increasing the voltage.

As best illustrated in FIG. 3, a feedback loop 63 is applied in the first stage amplifier 38 to continuously monitor its own output voltage to ensure that it is substantially similar to its input voltage. This circuit arrangement allows the use of readily available, low cost components, for the rest of the electronics in the EMG device.

With the electrode assembly design of the present invention, the output signal from this first stage amplifier 38 is used for multiple purposes. First, the output signal from this first stage is connected to other, low impedance amplifier stages within the signal-processing unit at the end of the shielded cable (FIGS. 2 and 3). For instance, the signal input 59 of the low impedance second stage amplifier 62 is electrically coupled to the signal output 41 of the high impedance, first stage amplifier.

Second, the output voltage from this first stage amplifier 38 is applied to the shield conductor 37 of the shielded transmission line 31 (e.g., the outer conductor of a shielded co-axial cable (FIG. 2). The electrode assembly signal passes through the center conductor of this same shielded cable. At the opposed electrode assembly end, the outer conductor 37 of the shielded cable 31 is electrically coupled to the corresponding "guard" device 28 located within second circuitry layer 43 (FIG. 1) of the electrode apparatus 23. A "guard" conductor thus protects each of the signal pickup conductors.

Noise Shielding

Without the guard design of the present invention, the signal transmission path ending at the input to the first stage amplifier 38 would be the sole conductor. This guard design places the guard circuit 64, a second conductor, between the signal transmission path 65 and the source of the ambient electrical field (FIG. 3). The capacitance of the guard circuit, where it comes in contact with passing electrical fields, is very close to that of the original signal path. Therefore, the magnitude of the alternating current induced by the electric field is also very close to that of the alternating current which would have been induced in the original signal path.

The impedance (reactive capacitance) of the guard circuit, however, is very low (e.g., in the range of between about $10^4$ ohms to about $10^6$ ohms) compared to the impedance of the signal path circuit (e.g., in the range of between about $10^8$ ohms to about $10^{10}$ ohms), the second stage amplifier 62 it connects to may be a lower impedance amplifier. Therefore, the voltage induced into the guard circuit is very low compared with the voltage that would have been induced into the signal path circuit without the guard.

When the outer conductor 37 of the shielded co-axial cable 31 (i.e., the transmission line 31) is electrically connected with second circuit layer 43 of the electrode apparatus 23, the resulting conductor "guards" the sensed biosignal by intercepting stray electrical fields before they can reach the signal electrode device 25 or the associated transmission conductor 36 in the center of the shielded cable 31. The "guard" circuit is connected to the low impedance output of the first stage amplifier 38. The application ensures that the output voltage of the first stage amplifier closely "follows" the signal voltage from the high impedance pickup, regardless of the effect of passing electrical fields.

The "guard" need not completely surround the signal carrying wire. That is, the circuitry of the guard devices 28–30 (FIG. 1) needs only to be positioned between the signal transmission portion 55 of the electrode device 25 and the source of the undesired ambient electrical field. However, to accommodate different positional arrangements of the electrode apparatus 23 on the body contours, the surface area footprint of the circuitry of the guard device 28, at any one location, is at least the same if not slightly larger than that, at the corresponding location, of the signal transmission portion 55 of the electrode device 25. Since the first sheet material 35 is relatively thin, the guard device is virtually seated atop the corresponding electrode device.

By way of example, one or more of the guard device 28–30 may include a guard conductor portion 66–68, corresponding to the respective contact portion 47–49, which is electrically coupled to a shield conductor portion 70–72, corresponding to the remaining respective signal transmission portions 55–58 of the electrode devices 25–27. The shield conductor portions 70–72, as best shown in FIG. 1, preferably have a footprint (i.e., a pattern and a width) that is substantially similar to that of the corresponding signal transmission portions 55–58. However, the footprint of the guard conductors portions 66–68 are larger than that of the corresponding contact portions 47–49 to ensure proper shielding. In one example, the contact portions may have a width dimension in the range of about 1 mm and length dimension in the range of about 1 cm, while the guard conductor portions may have similar or slightly larger width and length dimensions.

As shown in FIGS. 1 and 2, the guard device extends into the electrode apparatus 23 itself in the form of the second circuitry layer 43 of conductive material connected to the outer "guard" conductor of the transmission line 31. For example, a flexible electrode apparatus 23 with three separate "pickup" or sensing areas in the exposed surface of the second sheet material 45, would require a separate "guard" for each pickup. In this example the connector between the shielded cable and the electrode assembly would need six contacts.

Reducing Effective Capacitance

A "guard" circuit has a second, equally desirable effect. It is able to reduce the effective capacitance of a shielded signal path. For example, in some applications, a very long signal path between the electrode assembly and the input amplifier is desired. A ten-foot cable having a capacitance of 30 Pico farads per foot would have 300 Pico farads of capacitance between the inner conductor 36 and outer conductor 37 of the co-axial cable 31. A high impedance signal source cannot charge or discharge this much capacitance very quickly. If the outer conductor 37 of the shielded cable 31 were simply "grounded", the result would be an electrode assembly that would only be able to sense very low frequency signals (on the order of one to 10 Hertz.) However, the EMG signals are much higher in frequency, typically in the hundreds of Hertz, and would therefore be significantly attenuated by the capacitive "loading" of such a shielded cable.

In accordance with the present invention, by applying a high impedance, first stage amplifier 38 to "drive" the outer conductor 37 of the shielded cable 31, the electrical potential of the outer conductor 37 replicates that of the inner conductor 36 at the center of the co-axial cable. The potential difference between the inner and outer conductors remains substantially constant, meaning that the co-axial cable capacitance is not being charged and discharged by the electrode apparatus 23. The capacitive "loading" of the co-axial cable is thereby reduced, and the cable capacitance does not absorb nearly as much of the signal current from the electrode apparatus 23, despite the capacitance that exists between the inner and outer conductors of the shielded cable. This follows from the fact that this design uses an input first stage amplifier with a very high current gain, rather than voltage amplifier.

For example, a CMOS amplifier requires only approximately one Pico ampere ($10^{-12}$ amperes) of current input to produce an output of a milliampere ($10^{-3}$ amperes) or more. This represents substantially a current gain. The first stage amplifier current gain is the factor by which the cable capacitance is reduced. Using this technique, a small electrode assembly can be used to successfully detect millivolt level signals in the hundreds of Hertz through 10 feet of relatively high capacitance shielded cable without significant signal loss.

What is claimed is:

1. A flexible, surface electromyographic electrode apparatus for use on a surface of biological tissue to measure bio-electric signals thereof, said electrode apparatus comprising:

a first conductive electrode device having a contact portion adapted to directly contact the surface of the biological tissue to receive and transmit bio-electric signals, and a signal transmission portion carrying the bio-electric signal and electrically coupled to the contact portion;

a first conductive guard device positioned substantially adjacent to and substantially over said electrode device such that the measured bio-electric signal passing therethrough is substantially shielded from ambient electric fields generated from sources external to said electrode apparatus;

a substantially non-conductive, flexible, first sheet material positioned between said electrode device and said guard device to substantially prevent conductive contact therebetween;

a substantially non-conductive, flexible, second sheet material positioned between said contact portion and said signal transmission portion to substantially prevent conductive contact therebetween; and a conductive lead extending through said second sheet material to electrically couple the contact portion to the signal transmission portion.

2. The electrode apparatus according to claim 1, further including:

a substantially non-conductive, flexible, third sheet material positioned over said conductive guard device and mounted to said first sheet material in a manner enclosing said guard device therebetween, and said first sheet material being mounted to said second sheet material in a manner enclosing said signal transmission portion of the electrode device therebetween.

3. The electrode apparatus according to claim 1, wherein said contact portion of said electrode device includes a contact footprint, and said signal transmission portion of said electrode device includes a signal transmission footprint, and said guard device includes a guard conductor portion having a guard conductor footprint, and a shield conductor portion having a shield conductor footprint, said guard device being positioned and oriented such that when the electrode apparatus is operably mounted on the biological tissue, the guard conductor footprint of the guard conductor portion at least extends over the contact footprint of the electrode contact portion, and the shield conductor footprint of the shield conductor at least extends over the signal transmission footprint of said electrode signal transmission portion.

4. The electrode apparatus according to claim 3, wherein said guard conductor footprint of said guard conductor portion extends beyond the contact footprint of said contact portion.

5. The electrode apparatus according to claim 4, further including:

a substantially non-conductive, flexible, third sheet material positioned over said conductive guard device and mounted to said first sheet material in a manner enclosing said guard device therebetween, and said first sheet material being mounted to said second sheet material in a manner enclosing said signal transmission portion of the electrode device therebetween.

6. The electrode apparatus according to claim 1, further including:

a second conductive electrode device adapted to directly contact the surface of the biological tissue, at a location spaced-apart from said first conductive electrode device, to receive and transmit a respective bio-electric signal;

a second conductive guard device positioned substantially adjacent and substantially over said second conductive electrode device such that the respective measured bio-electric signal passing therethrough is substantially shielded from ambient electric fields generated from said sources external to said electrode apparatus; and said first sheet material further positioned between said second conductive electrode device and said second conductive guard device to substantially prevent conductive contact therebetween.

7. The electrode apparatus according to claim 6, wherein said second conductive electrode device having a respective contact portion adapted to directly contact the surface of the biological tissue, and a respective signal transmission portion carrying the respective bio-electric signal and electrically coupled to the respective contact portion thereof.

8. The electrode apparatus according to claim 7, wherein each said contact portion of the first and second electrode device includes a respective contact footprint, and each said signal transmission portion of the first and second electrode device includes a respective signal transmission footprint, and each said guard device includes a respective guard conductor portion having a respective guard conductor footprint, and a respective shield conductor portion having a respective shield conductor footprint, each respective guard device being positioned and oriented such that when the electrode apparatus is operably mounted on the biological tissue, the respective guard conductor footprint of the respective guard conductor portion at least extends over the respective contact footprint of the respective electrode contact portion, and the respective shield conductor footprint of the respective shield conductor at least extends over the respective signal transmission footprint of the respective electrode signal transmission portion.

9. The electrode apparatus according to claim 8, wherein each guard conductor footprint of the respective guard conductor portion extends beyond the respective contact footprint of the respective contact portion.

10. An electrode assembly for use on a surface of biological tissue to measure bio-electric signals thereof, said electrode assembly comprising:

an electrode apparatus having an electrode device adapted to directly contact the surface of the biological tissue to receive and transmit original bio-electric signals sensed from the biological tissue having an original first voltage and an original minute first current;

a shielded signal transmission line having a signal transmission conductor electrically coupled at one portion to the electrode device for transmission of said bio-electric signals, and a shield conductor electrically coupled to the electrode apparatus and arranged to substantially shield the transmission line from ambient electric fields generated from sources external to said transmission line;

a high impedance amplifier device having a signal input and a signal output, said signal input being electrically coupled to another portion of the signal transmission conductor for receipt of the transmitted bio-electric signals, said signal output being electrically coupled to the shield conductor, in a feedback loop, for receipt of at least a portion of the transmitted bio-electric signals, such that the voltage of the signals at said signal input of the high impedance amplifier device is maintained substantially equal to the voltage of the signals output from said signal output thereof; and a low impedance amplifier device having a signal input and a signal output, said signal input being electrically coupled to the signal output of the high impedance amplifier device for receipt of substantially the remaining portion of the transmitted bio-electric signals.

11. The electrode assembly according to claim 10, wherein said high impedance amplifier has a relatively high impedance in the range of about $10^8$ ohms to about $10^{10}$ ohms.

12. The electrode assembly according to claim 10, wherein said high impedance amplifier and said low impedance amplifier have relative high and low impedance, respectively, such that the bio-electric signals delivered from said output of said high impedance amplifier have a second current increased over said first minute current, and a second voltage substantially similar to the original first voltage of the original bio-electric signals.

13. The electrode assembly according to claim 12, wherein said high impedance amplifier has a relatively high impedance in the range of at least about $10^8$ ohms to at least about $10^{10}$ ohms, and said low impedance amplifier may have an impedance in the same range of about $10^4$ ohms to about $10^6$ ohms.

14. The electrode assembly according to claim 13, wherein said first minute current of the original bio-electric signals is in the range of about $10^{-14}$ amps to about $10^{-12}$ amps, while the second current is in the range of about $10^{-9}$ amps to about $10^{-6}$ amps, and said first original voltage of the original bio-electric signals is in the range of about $10^{-3}$ volts to about $10^{-3}$ volts, while the second voltage current is in the range of about $10^{-3}$ volts to about $10^{-1}$ volts.

15. The electrode assembly according to claim 10, wherein said shielded transmission line includes a shield cable wherein said signal transmission conductor is the central conductor, and said shield conductor is the outer conductor.

16. The electrode assembly according to claim 10, wherein said electrode assembly includes a guard shield situated over said electrode device to substantially shield the electrode device from said ambient electric fields generated from sources external thereto.

17. An electromyographic surface electrode assembly for use on a surface of biological tissue to measure bio-electric signals thereof, said electrode assembly comprising:

a flexible, surface electromyographic electrode apparatus including a conductive electrode device having a contact portion adapted to directly contact the surface of the biological tissue to receive and transmit bio-electric signals sensed from the biological tissue having an original first voltage and an original minute first current, and a signal transmission portion carrying the bio-electric signals and having one end electrically coupled to the contact portion;

a conductive guard device positioned substantially adjacent and substantially over said electrode device such that the measured bio-electric signal passing therethrough is substantially shielded from ambient electric fields generated from sources external to said electrode apparatus; and a substantially non-conductive, flexible, first sheet material positioned between said electrode device and said guard device to substantially prevent conductive contact therebetween; and a substantially non-conductive, flexible, second sheet material positioned between said contact portion and said signal transmission portion to substantially prevent conductive contact therebetween; and a conductive lead extending through said second sheet material to electrically couple the contact portion to the signal transmission portion;

a co-axial cable having an inner conductor and an outer conductor shielding the inner conductor, at one portion of said co-axial cable, said inner conductor being electrically coupled to an opposite end of the signal transmission portion of the electrode device for transmission of said bio-electric signals, and said outer conductor being electrically coupled to the guard device to substantially shield the inner conductor from said ambient electric fields generated from sources external thereto; and a high impedance amplifier device having a signal input and a signal output, said signal input being electrically coupled to the inner conductor of the co-axial cable at another portion thereof for receipt of the transmitted bio-electric signals, said signal output being electrically coupled to the outer conductor of the co-axial cable, in a feedback loop, for receipt of at least a portion of the transmitted bio-electric signals, such that the voltage of the signals at said signal input of the high impedance amplifier device is maintained substantially equal to the voltage of the signals output from said signal output thereof.

18. The electrode assembly according to claim 17, further including:

a substantially non-conductive, flexible, third sheet material positioned over said conductive guard device and mounted to said first sheet material in a manner enclosing said guard device therebetween, and said first sheet material being mounted to said second sheet material in a manner enclosing said signal transmission portion of the electrode device therebetween.

19. The electrode assembly according to claim 17, wherein said contact portion of said electrode device includes a contact footprint, and said signal transmission portion of said electrode device includes a signal transmission footprint, and said guard device includes a guard conductor portion and a shield conductor portion having one end electrically coupled to the guard conductor portion, and an opposite end electrically coupled to the outer conductor of the co-axial cable, said guard conductor having a guard conductor footprint, and a shield conductor portion having a shield conductor footprint, said guard device being positioned and oriented such that when the electrode apparatus is operably mounted on the biological tissue, the guard conductor footprint of the guard conductor portion at least extends over the contact footprint of the electrode contact portion, and the shield conductor footprint of the shield conductor at least extends over the signal transmission footprint of said electrode signal transmission portion.

20. The electrode assembly according to claim 17, wherein said electrode apparatus includes a number of conductive electrode devices each adapted to directly contact the surface of the biological tissue, at locations spaced-apart from one another, each electrode device being adapted to receive and transmit respective bio-electric signals;

a number of conductive guard devices each positioned substantially adjacent and substantially over a respective, corresponding conductive electrode device such that the respective measured bio-electric signals passing therethrough are substantially shielded from ambient electric fields generated from said sources external to said electrode apparatus; and said first sheet material further positioned between said number of conductive electrode devices and said number of conductive guard devices to substantially prevent conductive contact therebetween.

21. The electrode assembly according to claim 20, wherein each said conductive electrode device having a respective contact portion adapted to directly contact the surface of the biological tissue, and a respective signal transmission portion carrying the respective bio-electric signals and electrically coupled to the respective contact portion thereof.

22. The electrode assembly according to claim 21, wherein a said substantially non-conductive, flexible, second sheet material is positioned between the respective contact portion and the respective signal transmission portion to substantially prevent conductive contact therebetween; and further including:

a respective conductive lead extending through said second sheet material to electrically couple the respective contact portion to the respective signal transmission portion.

23. The electrode assembly according to claim 21, wherein each respective contact portion of the respective electrode device includes a respective contact footprint, and each respective signal transmission portion of the respective electrode device includes a respective signal transmission footprint, and each respective guard device includes a respective guard conductor portion having a respective guard conductor footprint, and a respective shield conductor portion having a respective shield conductor footprint, each respective guard device being positioned and oriented such that when the electrode apparatus is operably mounted on the biological tissue, the respective guard conductor footprint of the respective guard conductor portion at least extends over the respective contact footprint of the respective electrode contact portion, and the respective shield conductor footprint of the respective shield conductor at least extends over the respective signal transmission footprint of the respective electrode signal transmission portion.

24. The electrode assembly according to claim 23, wherein each guard conductor footprint of the respective guard conductor portion extends beyond the respective contact footprint of the respective contact portion.

25. An electromyographic surface electrode assembly for use on a surface of biological tissue to measure bio-electric signals thereof, said electrode assembly comprising:

a flexible, surface electromyographic electrode apparatus including
a conductive electrode device adapted to directly contact the surface of the biological tissue to receive and transmit bio-electric signals sensed from the biological tissue having an original first voltage and an original minute first current;
a conductive guard device positioned substantially adjacent and substantially over said electrode device such that the measured bio-electric signal passing therethrough is substantially shielded from ambient electric fields generated from sources external to said electrode apparatus; and
a substantially non-conductive, flexible, first sheet material positioned between said electrode device and said guard device to substantially prevent conductive contact therebetween;

a co-axial cable having an inner conductor and an outer conductor shielding the inner conductor, at one portion of said co-axial cable, said inner conductor being electrically coupled to the electrode device for transmission of said bio-electric signals, and said outer conductor being electrically coupled to the guard device to substantially shield the inner conductor from said ambient electric fields generated from sources external thereto;

a high impedance amplifier device having a signal input and a signal output, said signal input being electrically coupled to the inner conductor of the co-axial cable at another portion thereof for receipt of the transmitted bio-electric signals, said signal output being electrically coupled to the outer conductor of the co-axial cable, in a feedback loop, for receipt of at least a portion of the transmitted bio-electric signals, such that the voltage of the signals at said signal input of the high impedance amplifier device is maintained substantially equal to the voltage of the signals output from said signal output thereof; and a low impedance amplifier device having a signal input and a signal output, said signal input being electrically coupled to the signal output of the high impedance amplifier device for receipt of substantially the remaining portion of the transmitted bio-electric signals.

26. The electrode assembly according to claim 25, wherein said high impedance amplifier and said low impedance amplifier have relative high and low impedance, respectively, such that the bio-electric signals delivered from said output of said high impedance amplifier have a second current increased over said first minute current, and a second voltage substantially similar to the original first voltage of the original bio-electric signals.

27. The electrode assembly according to claim 26, wherein said high impedance amplifier has a relatively high impedance in the range of at least about $10^8$ ohms to at least about $10^{10}$ ohms, and said low impedance amplifier may have an impedance in the same range of about $10^4$ ohms to about $10^6$ ohms.

* * * * *